United States Patent [19]
Warfield, Jr.

[11] Patent Number: 5,735,077
[45] Date of Patent: Apr. 7, 1998

[54] CORN HYBRID EVALUATION

[76] Inventor: Thomas C. Warfield, Jr., 2276 Valley View Pl., Decatur, Ill. 62522

[21] Appl. No.: 764,520

[22] Filed: Dec. 12, 1996

[51] Int. Cl.$^6$ .............................. A01B 79/00; A01C 1/00; A01H 1/04
[52] U.S. Cl. .................. 47/58; 47/DIG. 1; 800/DIG. 56
[58] Field of Search ..................... 47/58, 14, 15, 47/16, DIG. 1; 800/200, DIG. 1, DIG. 56

[56] References Cited

U.S. PATENT DOCUMENTS 5,097,095  3/1992  Rosenbrook ........................... 800/200

OTHER PUBLICATIONS

Fox RH; Selection For Phosphorus Efficiency In Corn; Commun. Soil Sci. Plant Anal., 9(1), 1978, 13–38 (Abstract Only), 1978.

Misra et al.; Evaluation of Partially Acidulated Rock Phosphate In A Lateritic Soil; Indian J. Agr. Sci., 39(4), 1969, 353–361 (Abstract Only), 1969.

*Primary Examiner*—David T. Fox
*Assistant Examiner*—Kent L. Bell
*Attorney, Agent, or Firm*—Philip L. Bateman

[57] ABSTRACT

A corn hybrid is evaluated by a seven-step method. The first step is to obtain a quantity of kernels of the corn hybrid to be evaluated. The kernels are then planted uniformly in a series of soil pots. The kernels in the pots are exposed to uniform germinating and growing conditions in an enclosed area so the kernels develop into seedlings. The most advanced seedling in each pot is selected and the other seedlings removed. The selected seedlings are then exposed to uniform growing conditions so they develop into mature plants. Various physical properties of the plants are then measured and compared to the corresponding physical properties of other corn hybrids.

9 Claims, No Drawings

CORN HYBRID EVALUATION

FIELD OF THE INVENTION

This invention relates to the cultivation of corn. More particularly, this invention relates to the evaluation of corn hybrids.

BACKGROUND OF THE INVENTION

Corn is the most important crop grown in the United States and is the second largest crop grown in the world. A corn plant begins life as a seed, also known as a kernel. The kernel has three main parts: (1) an embryo, or germ, that develops into the plant; (2) an endosperm consisting primarily of starch that is used for energy by the embryo; and (3) a seed coat. After planting in the ground, the kernel develops into a seedling and then into a mature plant. A mature corn plant consists of roots, an upright stalk, leaves, one or more ears (each consisting of hundreds of kernels on a cob), and a tassel. A typical corn plant grows to a height of about three meters and has a life span of about five months.

Various kinds of corn are grown. They differ from each other primarily in the starch composition of the endosperm in their kernels. Starch having straight chain molecules is known as amylose and starch having branched chain molecules is known as amylopectin. Dent corn is the most important kind commercially because of its high yields (the quantity of kernels harvested per acre). Other common kinds of corn include waxy maize (high amylopectin corn), high amylose corn, high oil corn, flint corn, flour corn, sweet corn, and popcorn.

A corn plant reproduces sexually. Male sex cells from pollen released by the tassel unite with female sex cells on the cob. Most of the pollen falls on other plants, but some self-pollination typically occurs. The fertilized sex cells develop into the kernels on the cob. Any unfertilized female sex cells result in empty spots on the cob.

Most corn grown in the United States, regardless of kind, is of a genetic type known as corn hybrid. Corn hybrid is produced by a lengthy breeding process which begins by growing selected corn plants under conditions where inbreeding occurs—the selected plants are fertilized only by other plants in the same selected group. The inbreeding process is continued for several generations until all the plants in the group have similar genetic compositions. The next step in the process is to cross two inbred varieties. The two varieties are planted in close proximity and the tassels of one of the varieties are removed. The plants with the removed tassels are fertilized by the other variety of plants. The resulting kernels from these plants are known as single-cross corn hybrids and have a genetic composition which is a combination of the two inbred varieties.

The development of more vigorous and higher yielding corn hybrids continues. When a new corn hybrid is produced, it is evaluated by planting it and comparing it to existing corn hybrids. The evaluation process typically used suffers from many disadvantages. First, the process requires the planting of large quantities of both the experimental corn hybrid (the new hybrid being evaluated) and the control corn hybrid (the hybrid being used for comparison). Second, the process lacks precision because it is so dependent upon variable environmental conditions. And third, the process is slow because the corn hybrid must be harvested before a comparison on yields can be made.

It would be highly desirable if a more accurate, less expensive, and faster corn hybrid evaluation method were available.

SUMMARY OF THE INVENTION

The general object of this invention is to provide an improved method of evaluating corn hybrids. More particular objects are to provide a corn hybrid evaluation method that is more accurate, less expensive, and faster than current methods.

I have invented a method of evaluating a corn hybrid. The method comprises: (a) obtaining a quantity of kernels of the corn hybrid to be evaluated; (b) planting the kernels uniformly in a plurality of soil pots, each pot containing an identical number of kernels and being identical in size; (c) exposing the kernels to uniform germinating and growing conditions in an enclosed area for a sufficient period of time to enable the kernels to develop into seedlings; (d) selecting one seedling in each pot based on its growth and removing the others; (e) exposing the selected seedlings to uniform growing conditions for a sufficient period of time to enable the seedlings to develop into mature plants; (f) measuring a physical property of the plants; and (g) comparing the measured physical property to the corresponding physical property of other corn hybrids.

This method is more accurate than current methods for several reasons, including the minimizing of the effects of variable environmental conditions. The method is less expensive because smaller quantities of seed are needed and less testing ground in a field is required. The method is also faster because an evaluation can be made before the plants are ready for harvesting.

DETAILED DESCRIPTION OF THE INVENTION

1. The Invention In General

This invention is a seven-step method for evaluating a corn hybrid. The method is characterized by the planting of kernels uniformly in pots that are then exposed to uniform growing conditions. After the kernels develop into seedlings, one seedling in each pot is selected (usually the most advanced seedling) and the other seedlings are removed. The selected seedlings are then exposed to uniform growing conditions and the seedlings develop into mature plants. One or more physical properties of the plants are then compared to the corresponding physical properties of other corn hybrids. Each step is discussed in more detail below.

2. Obtaining Corn Hybrid Kernels

The first step in the method is to obtain a quantity of kernels of the corn hybrid to be evaluated. The kernels are preferably in good to excellent condition and are typically provided by commercial seed companies. The number of kernels needed for evaluation is generally about 40 to 400, preferably about 60 to 200, and most preferably about 80 to 100. If the number of kernels is less than about 40, the accuracy of the evaluation is not as high as when a greater number is used. As the number increases past 400, the additional costs more than offset any marginal gains in accuracy.

All kinds of corn are suitable for evaluation with this method, including dent corn, waxy maize (high amylopectin corn), high amylose corn, high oil corn, flint corn, flour corn, sweet corn, and popcorn. Dent corn is the most common kind of corn evaluated because it is the most important commercially. Similarly, corn hybrid is the most common type of corn evaluated because it is the most important commercially.

3. Planting The Kernels In Pots

The second step is to plant the kernels uniformly in a series of soil pots. The term "uniformly" means that each kernel is planted in an identical, or nearly identical, environment so that environmental factors are minimized in the growth of the plant.

The type of soil pot used for planting is a non-critical matter of choice. Suitable pots include those made of peat, tar paper, burlap, plastic, ceramic, and the like. It is preferred that the soil pot decompose in the soil so the pot can be placed directly into the field without having to remove the soil from the pot. Removing soil from a pot can interfere with the growth of the plant in the soil. Pots made of peat, tar paper, and burlap are preferred for this reason. Peat pots are the most preferred because of their low cost, light weight, and wide availability.

The volume of the soil pot is about 300 to 3000 cm$^3$ (0.3 to 3 l) and preferably about 500 to 2000 cm$^3$ (0.5 to 2 l). If the volume is less than about 300 cm$^3$, the soil in the pot is insufficient to support a corn plant to the stage of growth needed for evaluation. Pots larger than about 3000 cm$^3$ are suitable, but are more expensive and more cumbersome than necessary. The pot preferably has a surface area of about 50 to 300 cm$^2$. It is preferred that the horizontal dimension (width or diameter as the case may be) of the pot is about the same as the vertical dimension (height). Commercial pots invariably exhibit this width-to-height relationship. If the width-to-height ratio is too great or too small, the pot is too shallow or too deep to allow the root system of the corn plant(s) to develop adequately. Peat pots are commercially available in both round and square shapes and with nominal sizes of 3 and 4 inches (e.g., a round three inch peat pot has a diameter of 3 inches and a height of 3 inches). The preferred peat pot is a 4 inch square size. This peat pot has a volume of about 1000 cm$^3$ (1 l) and a surface area of about 100 cm$^2$.

The pots are filled with good quality potting soil with a medium compaction. The potting soil is preferably at near neutral conditions (a pH of about 6.7 to 7.0) and contains the macronutrients (nitrogen, phosphorus, and potassium), the secondary nutrients (calcium, magnesium, and sulfur), and the micronutrients (iron, manganese, copper, zinc, molybdenum, chlorine, and boron) necessary to sustain plant growth. Peat and/or vermiculite are often added to potting soils to improve its drainage. The preferred potting soil is black soil (humus).

The same number of kernels are planted in each pot. The number is generally about 4 to 20. If the number is less than four, the seedlings in the pot are unlikely to represent a sufficiently broad spectrum of growth. If the number is greater than 20, it becomes difficult to plant the kernels uniformly. The preferred number of kernels per pot is about 6 to 12 and the most preferred number is about 8 to 10. The selection of a single seedling from a group of this number reduces the total number to about 10 to 20% of the original population.

The kernels are planted uniformly in each pot so that each kernel has the same opportunity for growth. The preferred arrangement is to plant the kernels at a depth of about 2 cm in an evenly-distributed circle with the germ side of the kernel up and the tip pointed to the center. A template may be used to ensure even spacing. Planting 8 kernels in a circle has the additional advantage that the kernels can be evenly spaced without a template. Four kernels are positioned at the 12, 3, 6, and 9 o'clock positions. The remaining four kernels are then positioned in between the first four.

4. Germinating And Growing Conditions

The next step in the method is to expose the kernels to uniform germinating and growing conditions. These conditions are preferably at or near the optimal conditions for germinating and growing because such conditions best reveal differences between kernels. The optimal conditions are to place the pots in a well ventilated greenhouse exposed to abundant sunlight. The term "greenhouse" includes any enclosed area where temperature and sunlight can be controlled and maintained. The pots are saturated with water and the ambient air temperature is set at 21° C. (70° F.). After 12 hours, the ambient air temperature is raised to 29° C. (85° F.). The pots are lightly watered periodically.

The kernels typically sprout in about three to four days. Emergence from the surface of the soil occurs about one day later. The emerging seedling has the appearance of a spike because its leaves are tightly wrapped. The conditions inside the greenhouse are maintained until the largest seedling in each pot is near the end of the spike stage, i.e., when the first leave begins to unravel.

5. Selecting The Seedlings

The fourth step in the method is to select one seedling in each pot and to remove the others. The selection is made based on growth. In most cases, the most advanced seedling in each pot is selected. However, it may be desirable for some purposes to select a different seedling, e.g., the least advanced seedling in each pot, the median seedling in each pot, etc. When selecting the most advanced seedling in each pot, the selection is preferably made when the most advanced seedling in each pot is near the end of the spike stage.

As previously discussed, the selection process preferably reduces the number of seedlings to about 10 to 20 percent of the original number. The selection process most preferably reduces the number to about 10 to 13 percent (the percentage reduction occurring when 1 out of 10 to 1 out of 8 are selected) of the original number. The selection of a single seedling ensures that each seedling in each pot is exposed to nearly identical growing conditions. If, for example, two seedlings were chosen in each pot, a pair of seedlings spaced far apart from each other in one pot would be favored over a pair of adjacent seedlings in another pot.

While in most cases, one and only one seedling is selected, there are some instances where two or more seedlings are selected in each pot. For example, if plant growth in clusters is important, selecting two or more seedlings will more accurately reflect the growth qualities of primary interest. In any event, the non-selected seedlings in each pot are carefully removed from the pots to avoid disturbing the selected seedlings. After removal, the seedlings are discarded.

6. Continued Growth

The fifth step is to expose the selected seedlings to uniform growing conditions for a sufficient period of time to enable them to develop into plants. Because of the size and space requirements, the step is typically conducted outdoors in a field. Assuming the pots are made of a material that decomposes, the pots are placed into the soil and the corn plant continues its growth in the field in much the same way as conventional field corn. Alternatively, if sufficient greenhouse space is available, the selected seedlings may simply be transferred to larger pots and growth continued there.

A preferred way of carrying out this step outdoors is to move the pots into a specially prepared field. The field is prepared by planting corn rows in an east-west direction with a four row planter. The rows are spaced apart a distance of about 75 cm. Two adjacent rows are planted in corn with spacing between kernels of about 20 cm. The next two rows are left blank. Then two more rows are planted, two more rows are blank, etc. The two planted rows are referred to as the "corn wall" and the adjacent spaces are referred to as the "alley." The alley has a width of about 225 cm. The field is typically planted about one to five days before the kernels being evaluated are planted in the pots. This ensures that the corn plants in the field are at about the same stage of growth as the plants in the pots.

Two trenches are dug along one of the interior corn walls, one along the south side and one along the north side of the corn wall. Each trench is centered about 25 cm away from the corn wall and is sized to accommodate the pots. The pots are then placed into the two trenches with a spacing of about 75 cm between pots. A series of individual holes along the corn wall can be dug with a tulip bulb planter or the like in place of the trenches. In either case, each pot is oriented so the seed leaf plane of the selected seedling is parallel to the corn row. Half of the pots are placed on the south side of the corn wall so they are exposed to maximum sunlight. The remaining half are placed to the north side and are exposed to minimal sunlight. The pots are watered and sprayed for insects as needed.

7. Measuring Physical Properties

The sixth step is to measure one or more physical properties of the plants being evaluated. If time is of the essence, a preliminary evaluation is possible before the plant reaches maturity. Alternatively, a preliminary evaluation can be used for screening. For example, if the preliminary evaluation reveals substandard performance, the remainder of the evaluation may be omitted. In most cases however, it is preferred to wait to measure properties of the mature plant. Physical properties that are advantageously measured include the following:

(a) Number of leaf tips emerged 40 days after emergence of first leaf
(b) Flowering date
(c) Number of silked shoots
(d) Leaf thickness of fifth, tenth, and fourteenth leaves
(e) Plant height
(f) Ear height
(g) Staygreen
(h) Ear grain weight
(i) Circumference of ear
(j) Number of kernels on ear
(k) Weight of 25 base kernels and 25 tip kernels
(l) Circumference and length of cob
(m) Weight of cob

8. Comparing To Other Corn Hybrids

The final step is to compare the measured physical properties to the corresponding physical properties of other corn hybrids. It is well within the skill of commercial seed companies to develop data bases of corn hybrids for comparison purposes. Computer software is advantageously used for this type of comparison. On the basis of this comparison, the corn hybrid being evaluated may be commercialized, used for further breeding, discarded, subjected to further testing, etc.

9. Theory

While not wishing to be bound by theory, it is believed that this method is so accurate for three primary reasons. The first reason is that this method provides extremely uniform growth conditions to the plants. Throughout the growth from kernel to seedling to mature plant, every plant in the evaluation is exposed to nearly identical conditions.

The second reason for the accuracy of this method is that it provides nearly ideal growing conditions. It has been discovered that differences between individual plants are best revealed under such conditions. Under slower growth conditions or under stress, growth among corn plants tends to even out. As an analogy, differences in the athletic abilities of a group of children is better revealed by having the children run a given distance at maximum speed than by having them walk the same distance.

The third reason for the accuracy of this method is that, by discarding the non-selected seedlings, only those kernels which developed optimally since fertilization are considered. A kernel's genetic make-up (its genotype) is fixed at the time of fertilization and this genotype imposes limits on the properties of the mature plant (its phenotype). However, the mature plant will not achieve these limits unless it is exposed to optimal conditions during embryo development (as part of the mother plant) and during its independent growth. Returning to the human analogy, it is known that a human's maximum height is fixed by his or her genes at the time of fertilization. But this height will not be achieved if the fetus receives less than optimal pre-natal care or if, after birth, the individual is exposed to less than optimal conditions for growth (diet, exercise, freedom from disease, etc.).

I claim:

1. A method of evaluating a corn hybrid, the method comprising:

(a) obtaining a quantity of kernels of the corn hybrid to be evaluated;
(b) planting the kernels in a plurality of soil pots under conditions that are uniform in terms of soil pot size, soil composition, number and spacing of the kernels in each pot, and depth and orientation of the kernels in the soil;
(c) exposing the kernels to germinating and growing conditions that are uniform and optimal in terms of sunlight, ventilation, temperature, and soil moisture level in an enclosed area for a sufficient period of time to enable the kernels to develop into seedlings;
(d) selecting the largest seedling in each pot and removing the others;
(e) exposing the selected seedlings to growing conditions that are uniform in terms of sunlight, ventilation, temperature, and soil moisture level for a sufficient period of time to enable the seedlings to grow;
(f) measuring a phenotypic trait of the plants; and
(g) comparing the measured phenotypic trait to the corresponding phenotypic trait of other corn hybrids.

2. The method of claim 1 wherein the quantity of kernels obtained is about 60 to 200.

3. The method of claim 2 wherein the soil pots are made of a decomposing material selected from the group consisting of peat, tar paper, and burlap.

4. The method of claim 3 wherein the soil pots have a volume of about 0.5 to 2 liters and a surface area of about 50 to 300 cm$^2$.

5. The method of claim 4 wherein about 6 to 12 kernels are planted in each soil pot.

6. The method of claim 5 wherein the kernels are evenly distributed in a circle.

7. The method of claim 6 wherein the pots are planted outdoors in a field immediately after the largest seedling in each pot is selected.

8. The method of claim 7 wherein the soil pots are made of peat.

9. The method of claim 8 wherein a plurality of phenotypic traits of the plants are measured and compared to the corresponding phenotypic traits of other corn hybrids.

* * * * *